(12) United States Patent
Deguchi et al.

(10) Patent No.: US 9,651,467 B2
(45) Date of Patent: May 16, 2017

(54) RAW MATERIAL FLUID DENSITY DETECTOR

(71) Applicants: TOKUSHIMA UNIVERSITY, Tokushima (JP); FUJIKIN INCORPORATED, Osaka (JP)

(72) Inventors: Yoshihiro Deguchi, Tokushima (JP); Masaaki Nagase, Osaka (JP); Ryousuke Dohi, Osaka (JP); Nobukazu Ikeda, Osaka (JP); Kouji Nishino, Osaka (JP); Michio Yamaji, Osaka (JP); Tadayuki Yakushijin, Osaka (JP)

(73) Assignees: TOKUSHIMA UNIVERSITY, Tokushima (JP); FUJKIN INCORPORATED, Osaka (JP)

( * ) Notice: Subject to any disclaimer, the term of this patent is extended or adjusted under 35 U.S.C. 154(b) by 17 days.

(21) Appl. No.: 14/888,841

(22) PCT Filed: Apr. 30, 2014

(86) PCT No.: PCT/JP2014/002376
§ 371 (c)(1),
(2) Date: Nov. 3, 2015

(87) PCT Pub. No.: WO2014/181527
PCT Pub. Date: Nov. 13, 2014

(65) Prior Publication Data
US 2016/0061704 A1    Mar. 3, 2016

(30) Foreign Application Priority Data

May 9, 2013    (JP) ................................. 2013-099081

(51) Int. Cl.
*G01N 9/00*    (2006.01)
*G01N 21/05*    (2006.01)
(Continued)

(52) U.S. Cl.
CPC ................. *G01N 9/00* (2013.01); *G01N 9/24* (2013.01); *G01N 21/05* (2013.01); *G01N 21/59* (2013.01);
(Continued)

(58) Field of Classification Search
CPC    G01N 9/00; G01N 9/24; G01N 21/05; G01N 21/59
(Continued)

(56) References Cited

U.S. PATENT DOCUMENTS 4,187,721 A * 2/1980 Smith .................. G01F 1/8413
73/32 A
6,161,875 A    12/2000 Yamaji et al.
(Continued)

FOREIGN PATENT DOCUMENTS

CA    2267453 A1    9/1999
CA    2690078 A1    12/2008
(Continued)

OTHER PUBLICATIONS

International Search Report, PCT/JP2014/002376, Jul. 22, 2014.

*Primary Examiner* — Seung C Sohn
(74) *Attorney, Agent, or Firm* — Studebaker & Brackett PC

(57) ABSTRACT

This invention is related to an optical-analysis-type raw material fluid density detector including a detector main body and a light oscillation unit and a light detection unit that are provided on the upper surface or the under surface of the detector main body, in which the detector main body has at least one recess formed in the upper surface and the under surface, a fluid flow path connecting a fluid inlet of the detector main body to the recess, a fluid flow path connecting the recesses to each other, and a fluid flow path connecting the recess to a fluid outlet of the detector main body;

(Continued)

the light oscillation unit is disposed in the recess that is closest to the inlet; and light detection units are disposed in the remaining recesses.

12 Claims, 5 Drawing Sheets

(51) Int. Cl.
*G01N 21/59* (2006.01)
*G01N 9/24* (2006.01)
*G01N 21/33* (2006.01)
*G01N 21/85* (2006.01)

(52) U.S. Cl.
CPC ............ *G01N 21/33* (2013.01); *G01N 21/85* (2013.01); *G01N 2201/08* (2013.01)

(58) Field of Classification Search
USPC ........................................................ 250/573
See application file for complete search history.

(56) References Cited

U.S. PATENT DOCUMENTS

| 6,987,565 | B2 | 1/2006 | Hirahara et al. |
| 2004/0056044 | A1 | 3/2004 | Hirahara et al. |
| 2007/0044816 | A1* | 3/2007 | Saito .................. B08B 3/00 134/1 |
| 2008/0221711 | A1* | 9/2008 | Trainer .............. G01N 15/0205 700/54 |
| 2010/0127217 | A1 | 5/2010 | Lightowlers et al. |

FOREIGN PATENT DOCUMENTS

| JP | H09-178652 A | 7/1997 |
| JP | H11-280967 A | 10/1999 |
| JP | 2004-108981 A | 4/2004 |
| JP | 2007-305945 A | 11/2007 |
| JP | 3155842 U | 12/2009 |
| JP | 2010-530067 A | 9/2010 |
| WO | 2008/152351 A1 | 12/2008 |

* cited by examiner

RAW MATERIAL FLUID DENSITY DETECTOR

TECHNICAL FIELD

The present invention relates to an improvement of a process fluid density meter for use in a raw material fluid supply system for a semiconductor manufacturing apparatus and the like, and particularly relates to an in-line optical-analysis-type raw material fluid density detector which achieves a size reduction and an in-line type of a sensor unit of a density meter and also enables maintenance of high transparency of a light transmission window and high cleanliness (resistance to particles) of the inside of a sensor which are stable over a long time period even in the case of a raw material fluid having high deposition properties, high photoreactivity, and corrosiveness.

BACKGROUND ART

The raw material fluid supply system for the semiconductor manufacturing apparatus and the like needs to supply a process raw material fluid with a stable density to a processing device in terms of improving the quality of a semiconductor product.

Thus, in the former raw material fluid supply system of this type, e.g., in a bubbling type raw material fluid supply system illustrated in FIG. 9, an optical-analysis-type density meter 22 is provided in the vicinity of a raw material vapor outlet of a raw material tank 21 of which temperature is controlled, and the temperature of the raw material tank 21, the flow rate of a carrier gas CG, the vapor pressure Po in the tank, and the like are adjusted by a density detection signal from the density meter 22, whereby a process gas 24 (for example, a process gas containing organometallic material steam, such as trimethyl gallium TMGa, stored in the tank 21) of a predetermined raw material density is supplied to a reactor 23.

FIG. 9 includes thermal mass flow controllers 25 and pressure adjusting devices 26 for the pressure in the tank.

Although density meters 22 having various kinds of configurations are practically used as the optical-analysis-type density meter 22, as illustrated in FIG. 10 (Japanese patent Laid-Open No. 9-178652) and FIG. 11 (Japanese Patent Laid-Open No. 2004-108981), almost the density meters 22 contain an optical cell (gas cell) 27 through which a gas G to be measured flows, a light source 28 which irradiates the inside of the optical cell 27 with light beams, a light receiving device 29 of the light beams passing through the inside of the optical cell 27, an arithmetic calculation device 30 which determines the absorbance from a signal of the light receiving device 29 to calculate the raw material density, and the like. The reference numeral 31 denotes a main pipe line and 32 denotes a branch pipe line.

The density meter 22 of FIG. 10 is configured so that a so-called absorbance of the gas in the optical cell 27 is measured and also the gas density is calculated by applying the Lambert-Beer law to the measurement result of the absorbance.

In the Japanese Patent Laid-Open No. 2004-108981, as illustrated in FIG. 11, an in-line sensor 33 containing an optical cell (light absorption cell) is fixed to the pipeline 31, and the luminous intensity of light transmitting through the optical cell is measured.

The optical-analysis-type density meter 22 and the in-line sensor 33 containing the optical cell (light absorption cell) 27 are known, and thus a detailed description thereof is omitted herein.

Thus, when measuring the raw material gas density, the optical cell 27 first needs to be connected and fixed to the pipeline 32 (or the pipeline 31). However, there are problems that it is not easy to secure the airtightness of a connecting portion between the optical cell 27 and the pipeline 32 (or the pipeline 31) and, for example, it is not easy to achieve connection and fixation having high airtightness by screw connection and a flange connection method employing usual packing materials and seal materials, which makes it actually impossible to achieve securing of airtightness performance (External leak of $1 \times 10^{-10}$ Pa·m$^3$/sec or less) demanded in the field of a semiconductor manufacturing apparatus.

In order to continuously perform stable gas density measurement over a long period of time, the transparency of the light transmission window of the optical cell 27 needs to be stable over a long period of time. When the transparency changes with time, the stable gas density measurement becomes difficult to achieve.

However, quartz glass has been used as a constituent material of the light transmission window in former density meters in many cases. Thus, when measuring the density of an organic raw material gas having high corrosiveness or high deposition properties, the light transmission window is corroded or the transparency decreases at an early stage due to the deposition of the raw material. Thus, a problem that stable measurement of the raw material gas density cannot be performed has remained unsolved.

On the other hand, various structures in the optical cell 27 also need to be firmly fixed and held to the main body of the optical cell 27 with high airtightness. Thus, inside the optical cell 27, various kinds of synthetic resin seal materials, silver brazing, gold brazing, and the like are used.

However, materials, such as synthetic resin seal materials, silver brazing, and gold brazing, in the optical cell 27 have risk of serving as emission sources which emits gas and particles contained in each material itself into the organic raw material gas, which actually poses a problem of a reduction in gas purity due to the emission of particles. Thus, in the gas supply systems for semiconductor manufacturing, the use of silver brazing or gold brazing is not desirable.

As described above, the use of the former optical-analysis-type density meter makes it difficult to reduce the size and the cost of facilities and also poses a large number of problems in maintaining gas airtightness, securing of stability of density measurement accuracy, maintenance of high gas purity, and the like. Particularly in the case of an organic raw material gas, the problems, such as the reduction in the transparency of the light transmission window resulting from the corrosiveness thereof, the reduction in the gas purity due to the seal members, the securing of airtightness, and the like, need to be solved as soon as possible.

CITATION LIST

Patent Literature

Patent Document 1: Japanese Laid-Open Patent Publication No. 9-178652
Patent Document 2: Japanese Laid-Open Patent Publication No. 2004-108981
Patent Document 3: Japanese Laid-Open Patent Publication No. 11-280967

SUMMARY OF INVENTION

Technical Problem

A main object of the present invention is to provide an in-line type raw material fluid density detector which solves the above-described problems in a raw material density meter for use in a former raw material fluid supply system and the like, i.e., (I) A simplification of the structure and a reduction in the size and the product cost of a density meter are not easy to achieve, (II) Stable and high-accuracy measurement of the raw material fluid density cannot be performed due to fluctuation of the transparency of a light transmission window, and the like, and which can stably and highly accurately measure the density without causing fluctuation of the transparency of a light transmission window over a long period of time even in the case of an organic raw material fluid with high corrosiveness and also can achieve size reduction and manufacturing at low cost.

Solution to Problem

As the basic configuration of the present invention, a first aspect of a raw material fluid density detector according to the present invention is an optical-analysis-type raw material fluid density detector comprising a detector main body 2 and a light oscillation unit 5a and a light detection unit 5b provided on the upper surface or the undersurface of the detector main body 2, wherein the detector main body 2 includes at least one recess 17 formed in the upper surface and the undersurface thereof; a fluid flow path 2a connecting a fluid inlet of the detector main body 2 to the recess 17, a fluid flow path 2b connecting the recesses 17 to each other, and a fluid flow path 2c connecting the recess 17 to a fluid outlet of the detector main body 2, the light oscillation unit 5a is disposed in at least one recess, and the light detection unit 5b is disposed in the remaining recess.

According to a second aspect of the raw material fluid density detector according to the first aspect of the present invention, the light oscillation unit includes a light transmission plate, a photodiode for light intensity detection, and a light source (optical fiber) for light oscillation, and the light detection unit includes a light transmission plate and a photodiode for light intensity detection in the raw material fluid density detector.

According to a third aspect of the raw material fluid density detector according to in the second aspect of the present invention, the light transmission plates disposed in the recesses formed in the detector main body are airtightly fixed using gasket type seals in the raw material fluid density detector.

A fourth aspect of a raw material fluid density detector according to the present invention is an optical-analysis-type raw material fluid density detector comprising a detector main body 2, a light oscillation unit 5a provided on the upper surface of the detector main body 2, a light detection unit 5b provided on the undersurface of the detector main body 2, recesses 17 provided in the upper surface and the undersurface of the detector main body 2 and connected to each other through a fluid flow path 2b, gasket type seals 6 attached into the recesses 17, a first fixing flange 14 and a second fixing flange 16 disposed facing the gasket type seals 6 and airtightly joined and fixed while holding the light transmission plates 11a, an optical fiber 9 and a photodiode 10 provided in the second fixing flange 16, and a holding and fixing body 12 airtightly fixing both the joined-and-fixed fixing flanges 14 and 16 into the recesses of the detector main body 2 through the gasket type seals 6.

A fifth aspect of a raw material fluid density detector according to the present invention is an optical-analysis-type raw material fluid density detector comprising a detector main body 2, a light oscillation unit 5a provided on the upper surface of the detector main body 2, and a light detection unit 5b provided on the undersurface of the detector main body 2, wherein the detector main body 2 includes a recess 17 provided in each of the upper surface and the undersurface thereof, a fluid flow path 2b connecting both the recesses 17 to each other, a fluid flow path 2a connecting a fluid inlet to the recess 17 in the upper surface, and a fluid flow path 2c connecting a fluid outlet to the recess 17 in the undersurface; and wherein the light oscillation unit 5a and the light detection unit 5b each have a gasket type seal 6 attached into a gasket accommodation portion 17a linked to the recess 17, a first fixing flange 14 including an insertion recess 14b having an inner circumferential surface having a stepwise narrowed diameter and disposed facing the gasket type seal 6, a light transmission plate 11a disposed at the deepest portion of the insertion recess 14b of the first fixing flange 14, a second fixing flange 16 airtightly joined and fixed to the insertion recess 14b while sandwiching the light transmission plate 11a by inserting of a projection portion 16b having a step-like outer circumferential surface into the insertion recess 14b of the first fixing flange 14, a photodiode 10 for light intensity detection disposed and fixed on the outside of the light transmission plate 11a in the second fixing flange 16, and a holding and fixing body 12 including a flange accommodation portion 12a accommodating both the fitted-and-fixed fixing flanges 14 and 16 at the center portion and airtightly fixing both the fixing flanges 14 and 16 accommodated in the flange accommodation portion 12a to the detector main body 2 through the gasket type seal 6 by cramping fixation bolts 8.

Regarding a sixth aspect of the raw material fluid density detector according to the fifth aspect of the present invention, a tip surface 16d of the projection portion 16b of the second fixing flange 16 and a bottom surface 14c of the insertion recess 14b of the first fixing flange 14 serve as a seal surface of the light transmission plate 11a.

Regarding a seventh aspect of the raw material fluid density detector according to the fifth aspect of the present invention, a bottom surface 14e of the gasket accommodation portion 14d of the first fixing flange 14 serves as a gasket seal surface.

Regarding an eighth aspect of the raw material fluid density detector according to the fifth aspect of the present invention, an optical fiber insertion hole 9a is provided in the second fixing flange 16 of the light oscillation unit 5a, and the photodiode 10 serves as a photodiode for detecting the intensity of reflected light from the light transmission plate 11a.

Regarding a ninth aspect of the raw material fluid density detector according to the fifth aspect of the present invention, the photodiode 10 provided in the second fixing flange 16 of the light detection unit 5b serves as a photodiode for detecting the intensity of transmission light from the light transmission plate 11a.

Regarding a tenth aspect of the raw material fluid density detector according to the fifth aspect of the present invention, another light detection unit 5b is provided at an interval on the upper surface of the detector main body 2; the recess 17 of the light detection unit 5b provided in the undersurface of the detector main body 2 and the recess 17 of the light detection unit 5b are connected to each other through the fluid flow path 2c; and the intensity of reflected light from the light transmission plate 11a of the light detection unit 5b provided on the undersurface is detected in the light detection unit 5b.

Regarding an eleventh aspect of the raw material fluid density detector according to the fifth aspect of the present invention, the raw material fluid is a depositing, high reactive, or corrosive organic raw material.

Regarding a twelfth aspect of the raw material fluid density detector according to the fifth aspect of the present invention, the light transmission plate 11a is formed of sapphire.

Advantageous Effects of Invention

According to the present invention, at least one recess 17 is formed in the upper surface and the undersurface thereof, a fluid flow path 2a connecting a fluid inlet of the detector main body 2 to the recess 17, a fluid flow path 2b connecting the recesses 17 to each other, and a fluid flow path 2c connecting the recess 17 to a fluid outlet of the detector main body 2 are provided, the light oscillation unit 5a is disposed in at least one recess, and the remaining light detection units 5b are disposed in the remaining recesses in the detector main body 2. Thus, an in-line type raw material density detector with a very simple configuration can be achieved.

Moreover, the light oscillation unit 5a and the light detection unit 5b have the gasket type seal 6 attached into the gasket accommodation portion 17a, the first fixing flange 14 having the insertion recess 14b disposed facing the same, the second fixing flange 16 airtightly joined and fixed to the first fixing flange 14 by inserting and press-fitting the projection portion 16b into the insertion recess 14b, the sapphire light transmission plate 11a airtightly held between both the flanges, and the holding and fixing body 12 which pressurizes and fixes both the flanges 14 and 16 to the detector main body 2. Thus, the structure of the light oscillation unit 5a and the light detection unit 5b can be simplified and also high airtightness can be held.

Furthermore, the light transmission window 11 is formed of sapphire, and thus, even in the case of a depositing, reactive, and corrosive fluid, the light transmittance does not decrease and stable high-accuracy density measurement can be achieved.

Moreover, since the gasket type seal is used, mixing of impurities into the fluid can be completely eliminated as compared with other seal structures employing synthetic resin seal materials, silver brazing materials, gold brazing materials, and the like.

In addition, the light transmission window which is the plate member 11 containing a brittle fracture material is sandwiched between the first fixing flange 14 and the second fixing flange 16 and also both the flanges are airtightly joined and fixed, and further both the joined and fixing flanges, to which the light transmission window is attached, are airtightly inserted into the recess 17 with the holding and fixing body 12 fixed to the main body 2, and thus the light transmission window can be airtightly, easily, and firmly held and fixed without using a seal material.

Thus, the raw material fluid density detector of the present invention demonstrates outstanding effects in terms of reducing the size and the cost of facilities, maintaining airtightness, securing of stability of density measurement accuracy, maintaining of high gas purity, and the like.

DESCRIPTION OF EMBODIMENTS

Hereinafter, embodiments of the present invention are described in detail with reference to the drawings.

Figure 1:
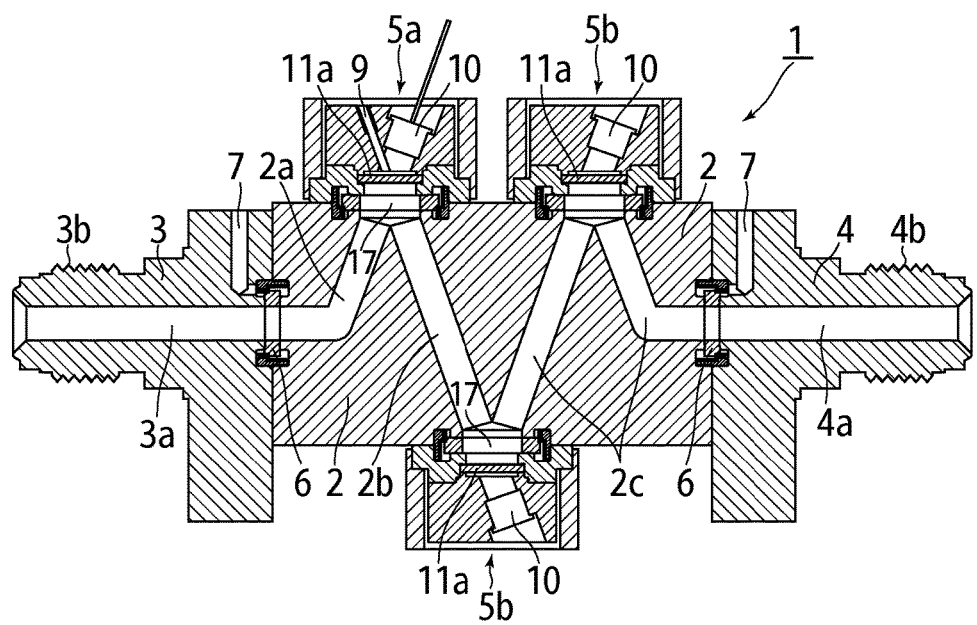
FIG. 1 A vertical cross-sectional view of a raw material fluid density detector according to an embodiment of the present invention.
Figure 2:
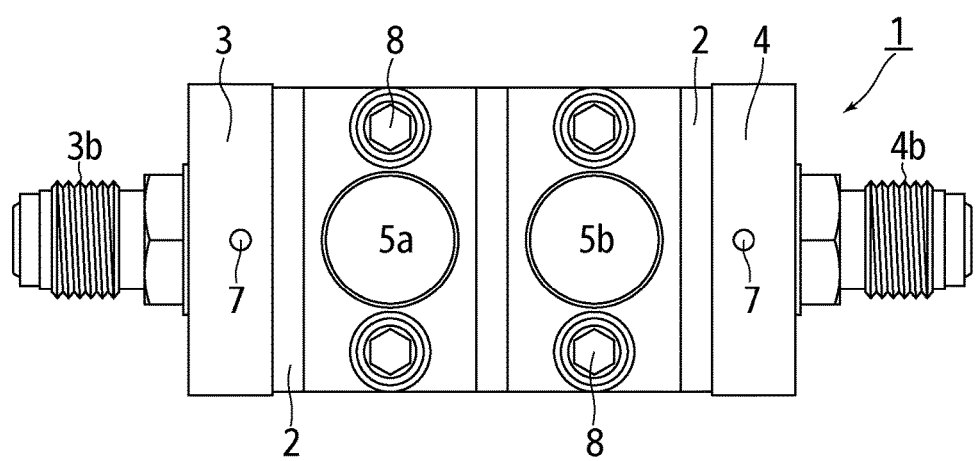
FIG. 2 A plan view of the raw material fluid density detector of FIG. 1.

FIG. 1 and FIG. 2 illustrate a raw material fluid density detector 1 according to a first embodiment of the present invention, and the raw material fluid density detector 1 is configured from a detector main body 2, an inlet block 3 and an outlet block 4 fixed to both sides thereof, a light oscillation unit 5a and a light detection unit 5b provided in parallel on the upper surface side of the detector main body 2, a light detection unit 5b provided on the undersurface side of the detector main body 2, and the like.

The detector main body 2, the inlet block 3, and the outlet block 4 are formed of stainless steel and the like, and fluid flow paths 2a, 2b, 2c, 3a, and 4a are provided in a communication manner. The inlet block 3 and the outlet block 4 are airtightly fixed to both sides of the detector main body 2 with bolts (not illustrated) via gasket type seals 6. The reference numerals 3b and 4b denote coupling portions, 7 denotes leakage inspection holes, and 8 denotes bolts for fixing the light oscillation unit 5a. The light detection unit 5b is also fixed with the fixation bolts 8 (not illustrated) in the same manner as in the light oscillation unit 5a.

The light oscillation unit 5a and the light detection unit 5b are disposed side by side at an interval on the upper surface side of the detector main body 2. Light of a predetermined wavelength in a visible region or an ultraviolet region from a light source device (not illustrated) containing a light source, a diffraction grating, a mirror, and the like enters a plate member 11 containing a brittle fracture material, i.e., a light transmission plate 11a containing a sapphire light transmission plate member, in the light oscillation unit 5a through an optical fiber 9.

Although a large part of the incident light transmits through the sapphire light transmission plate 11a to enter the fluid flow path 2a, the incident light is partially reflected by the sapphire light transmission plate 11a, and then the intensity of the reflected light is detected by the photodiode 10.

The light detection unit 5b is provided at an obliquely downward position with respect to the light oscillation unit 5a in such a manner as to face the light oscillation unit 5a on the undersurface side of the detector main body 2. The light entering from the light oscillation unit 5a through the fluid flow path 2b enters the photodiode 10 in the light detection unit 5b through the sapphire light transmission plate 11a, and then the light intensity of the incident light is detected.

Also in the sapphire light transmission plate 11a in the light detection unit 5b on the undersurface side of the detector main body 2, the incident light is partially reflected. However, the reflected light enters the light detection unit 5b on the upper surface side of the detector main body 2 through the fluid flow path 2c. Then, the intensity of the reflected light from the light detection unit 5b on the undersurface side is detected in the light detection unit 5b.

The light intensity detected in the light detection unit 5b on the undersurface side varies depending on the density and the like of a raw material fluid (fluid for process) which flows in the fluid flow path 2b. The detected light intensity signal is input into an arithmetic calculation device (not illustrated), and then the raw material density in the raw material fluid is calculated herein.

Generally, a raw material density C is calculated by the following expression (1) based on an absorbance A determined by a spectrum photometer.

$$A = \log_{10}(I_0/I) = \epsilon \times C \times l \quad (1)$$

In Expression (1), $I_0$ represents the incident light intensity from the light oscillation unit 5a, I represents the transmission light intensity (Intensity of incident light into the photodiode 10 of the light detection unit 5b), $\epsilon$ represents the molar absorptivity of the raw material, C represents the raw material density, and A represents the absorbance.

The light transmission characteristics of the light oscillation unit 5a and the light detection unit 5b change with time and the like but the changes in these light transmission characteristics appear as the changes in detection values of the photodiode 10 of the light oscillation unit 5a on the upper surface side and the photodiode 10 of the light detection unit 5b on the upper surface side, the photodiodes 10 which detect reflected light. Thus, the incident light intensity $I_0$ and the transmission light intensity I in Expression (1) above are compensated using the detection value of each of the photodiodes 10 of the light oscillation unit 5a and the light detection unit 5b on the upper surface side.

Figure 3:
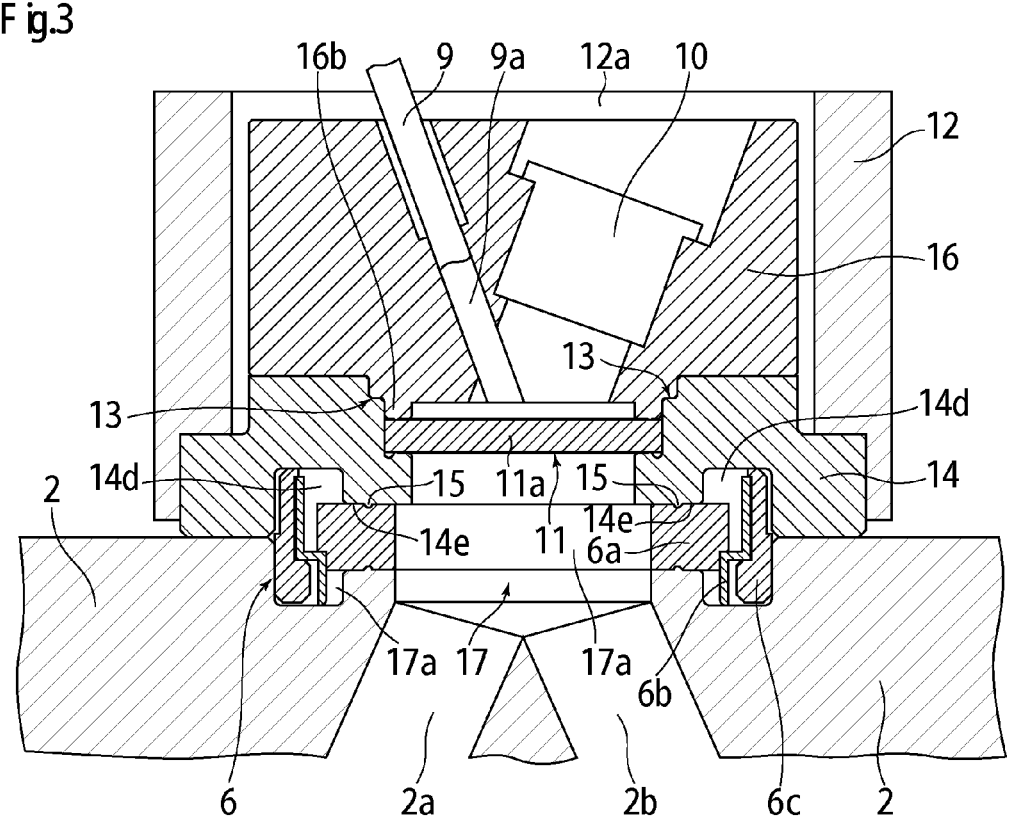
FIG. 3 A vertical cross-sectional view of a light oscillation unit of the raw material fluid density detector of FIG. 1.

The light oscillation unit 5a and the light detection unit 5b are completely the same in the structure and are configured from, as illustrated in FIG. 3, a holding and fixing body 12 which is formed of stainless steel and has a flange accommodation hole 12a at the center, a first fixing flange 14 provided on the outer surface of the detector main body 2, a second fixing flange 16, a sapphire light transmission plate 11a which is airtightly sandwiched and fixed between both the flanges 14 and 16, a photodiode 10 which is located above the light transmission plate 11a and is fixed to the second fixing flange 16, and the like.

More specifically, by press fitting a projection portion 16b of the second fixing flange 16 into the insertion recess 14b of the first fixing flange 14 with force of 8 to 12 N as described later, the second fixing flange 16 and the first fixing flange 14 are airtightly integrated in a state where the sapphire light transmission plate 11a is sandwiched and fixed therebetween with the tip surface 16d of the projection portion 16b and the bottom surface 14c of the insertion recess 14b as a seal surface.

By inserting the integrated second fixing flange 16 and first fixing flange 14 into the flange accommodation hole 12a of the holding and fixing body 12, and then pressurizing and fixing the holding and fixing body 12 to the detector main body 2 via the gasket type seals 6 with the fixation bolts 8, the light oscillation unit 5a and the light detection unit 5b are airtightly fixed to the detector main body 2.

FIG. 3 includes a recess 17 formed in the outer surface of the detector main body 2, a gasket 6a, a seal surface 13 between both the fixing flanges 14 and 16, a seal surface 14e between the gasket 6a and the first fixing flange 14, and an optical fiber insertion hole 9a.

In the embodiment of FIG. 1, the light oscillation unit 5a and the light detection unit 5b are provided at an interval on the upper surface side of the detector main body 2. However, it is a matter of course that the light detection unit 5b on the upper surface side is omitted and the recess 17 of the light detection unit 5b on the undersurface side and the fluid outlet side may be directly connected to each other by the fluid flow path 2c.

Furthermore, the light detection unit 5b can be provided on the upper surface side of the detector main body 2 and the light oscillation unit 5a can be provided on the undersurface side, i.e., the light oscillation unit 5a can be disposed in another recess in place of disposing the same in a recess closest to the inlet and another material, e.g., quartz glass and the like, can also be used in place of the sapphire light transmission plate 11a.

Figure 4:
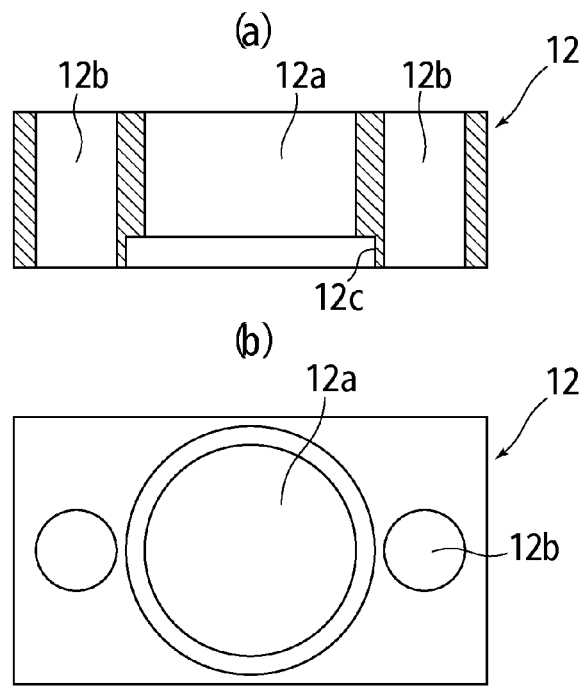
FIG. 4 A vertical cross-sectional view and a plan view of a holding and fixing body of the light oscillation unit of FIG. 3.

Specifically, in the holding and fixing body 12, as illustrated in FIG. 4, the flange accommodation hole 12a is provided in the central portion of a 12 to 15 mm thick square steel plate and insertion holes 12b for the fixation bolts 8 are provided in both sides thereof.

Moreover, a step portion 12c which is fitted to the upper surface of the outer circumferential portion of the first fixing flange 14 for pressurizing the same is formed in the lower end portion of the holding and fixing body 12. The diameter of the lower portion of the flange accommodation hole 12a is enlarged and is formed in the accommodation portion of the first fixing flange 14.

Figure 5:
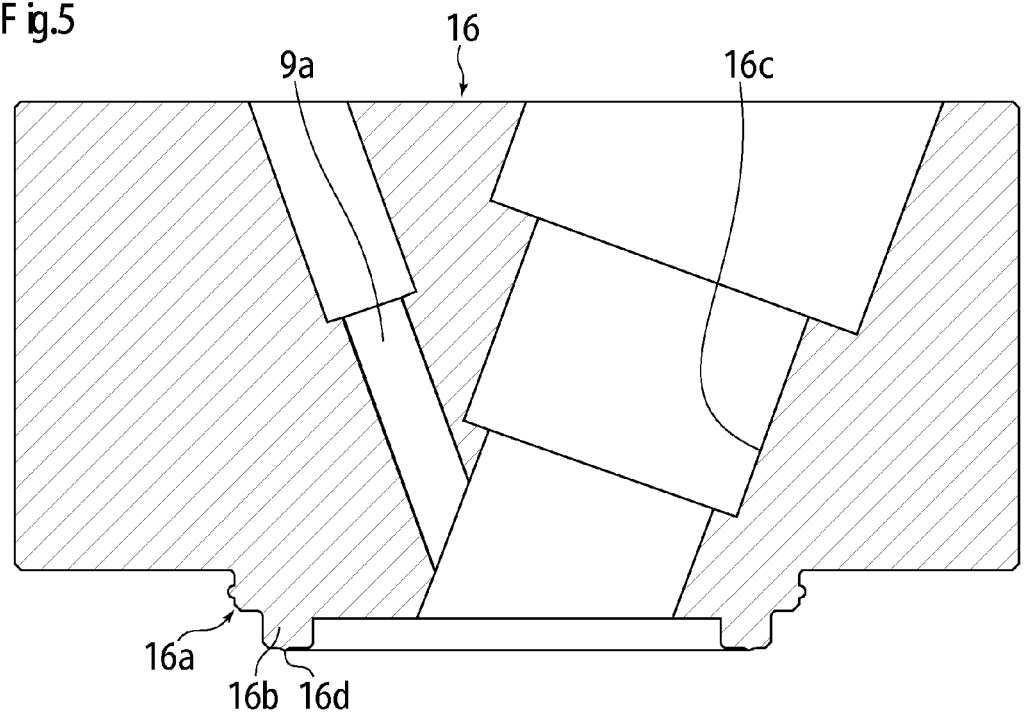
FIG. 5 A vertical cross-sectional view of a second fixing flange of the light oscillation unit of FIG. 3.

As illustrated in FIG. 5, the second fixing flange 16 is formed in the shape of a short cylinder formed of stainless steel and the central portion on one side thereof is formed in the projection portion 16b having a stepwise narrowed diameter by a two-step portion 16a.

The tip surface 16d of the tip portion of the narrowed projection portion 16b serves as the seal surface abutting on the thin light transmission plate 11a having a thickness of about 0.8 to 1.5 mm.

Figure 6:
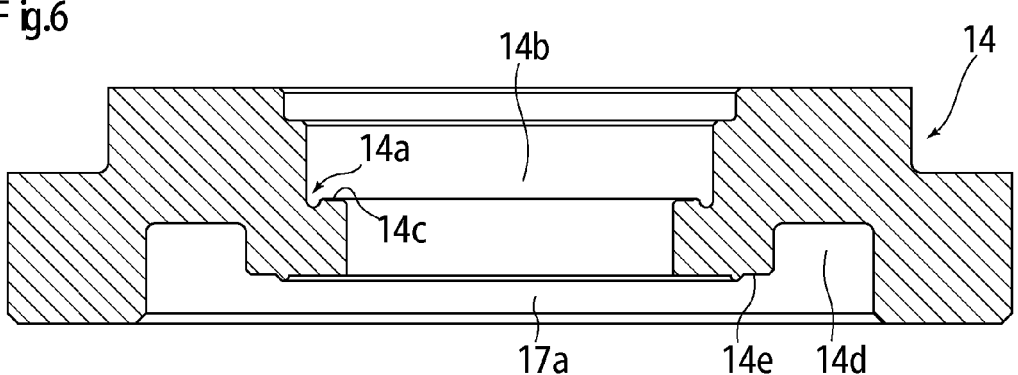
FIG. 6 A vertical cross-sectional view of a first fixing flange of the light oscillation unit of FIG. 3.

As illustrated in FIG. 6, the first fixing flange 14 is formed in a disk shape with stainless steel and is formed in the insertion recess 14b having a stepwise narrowed diameter by a three-step portion 14a in the central portion. Moreover, the insertion recess 14b is formed in such a manner as to penetrate and is connected to the recess 17 of the detector main body 2.

Furthermore, the middle portion of the three-step portion 14a forms an accommodation portion of the sapphire light transmission plate 11a, and the sapphire light transmission plate 11a is placed and fixed therein.

The accommodation portion 14d for the gasket 6a is formed in the undersurface side of the first fixing flange 14, and the upper half portion of the gasket type seal 6 is inserted and fixed therein.

Figure 7:
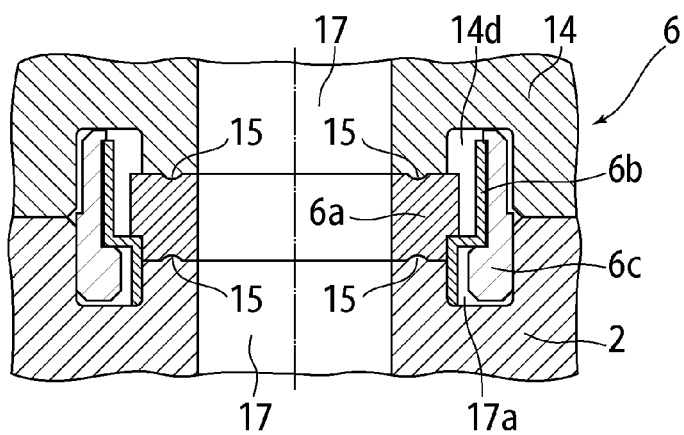
FIG. 7 A cross-sectional view showing the outline of a gasket type seal of the light oscillation unit of FIG. 3.

As illustrated in FIG. 7, the gasket type seal 6 is configured from the gasket accommodation portion 14d of the first fixing flange 14, the gasket accommodation portion 17a on the side of the detector main body 2, the ring-like gasket 6a, a ring-like retainer 6b, a ring-like guide ring 6c, and the like and is configured to be sealed double by the seal surfaces 15 and 15.

It is confirmed that the sapphire light transmission plate 11a constituting the light transmission window formed of the plate member 11 contains a brittle fracture material is a so-called single crystal of high purity alumina ($Al_2O_3$) formed with a thickness of 0.8 to 1.5 mm and has excellent abrasion resistance, corrosion resistance (chemical resistance), heat resistance, and the like, and thus the sapphire light transmission plate 11a is hardly corroded and degraded by organic raw material gas when used for semiconductor manufacturing and the optical transparency thereof is hardly changed.

Since the gasket type seal 6, the sapphire light transmission plate 11a, the photodiode 10, and the like are known, a detailed description thereof is omitted herein.

Next, a density detection test of the raw material fluid density detector 1 according to the present invention and the results thereof are described.

Figure 8:
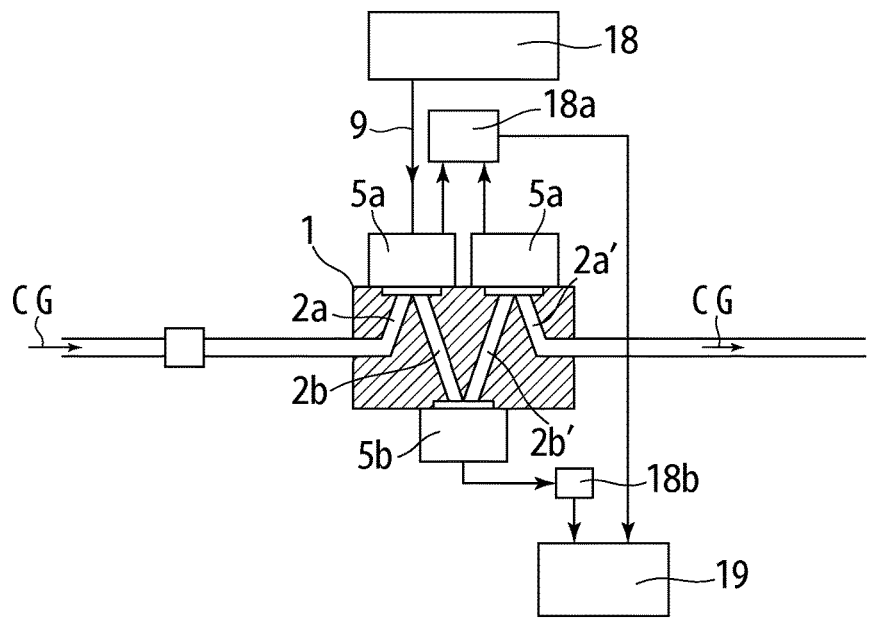
FIG. 8 A system diagram showing the outline of a testing system of a density meter according to the present invention.
Figure 9:
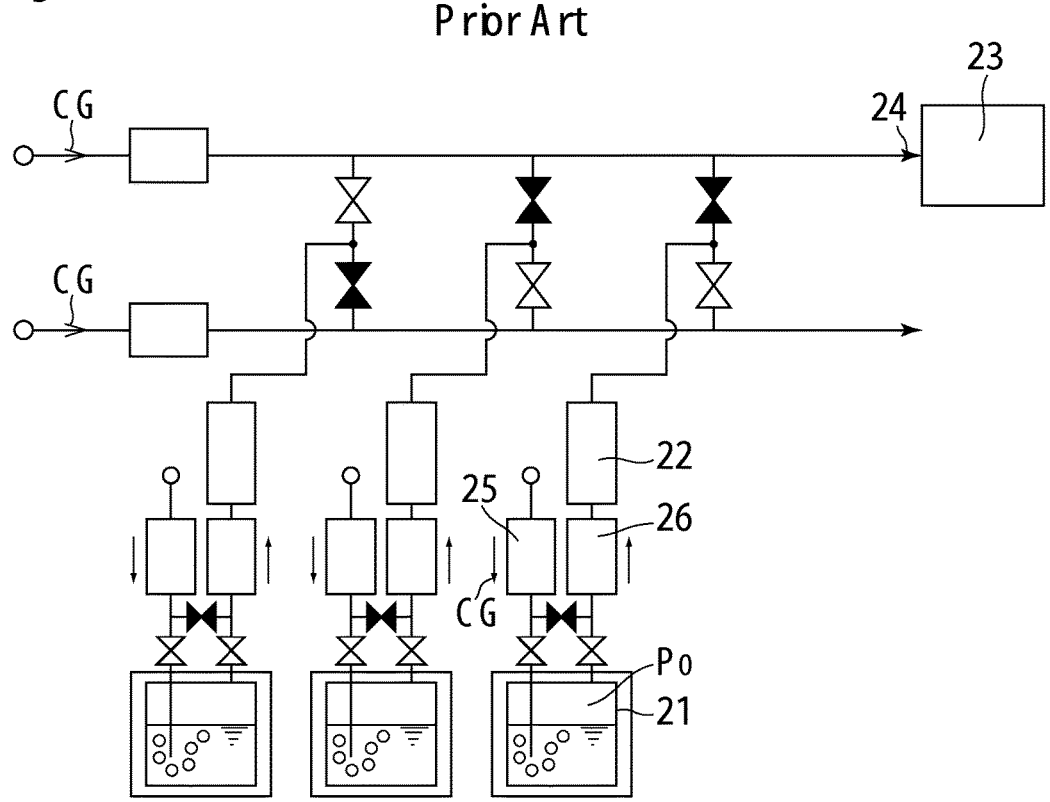
FIG. 9 A system diagram for explaining a former raw material gas supply device for semiconductor manufacturing apparatus.
Figure 10:
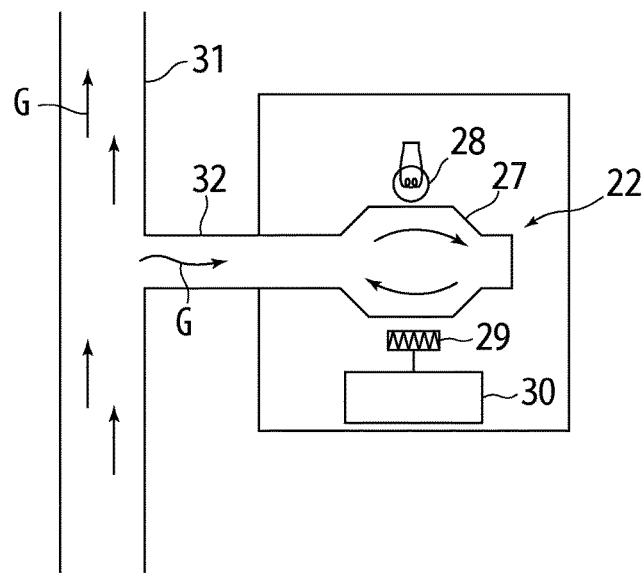
FIG. 10 A systematic view showing an example of use of a former gas density meter.
Figure 11:
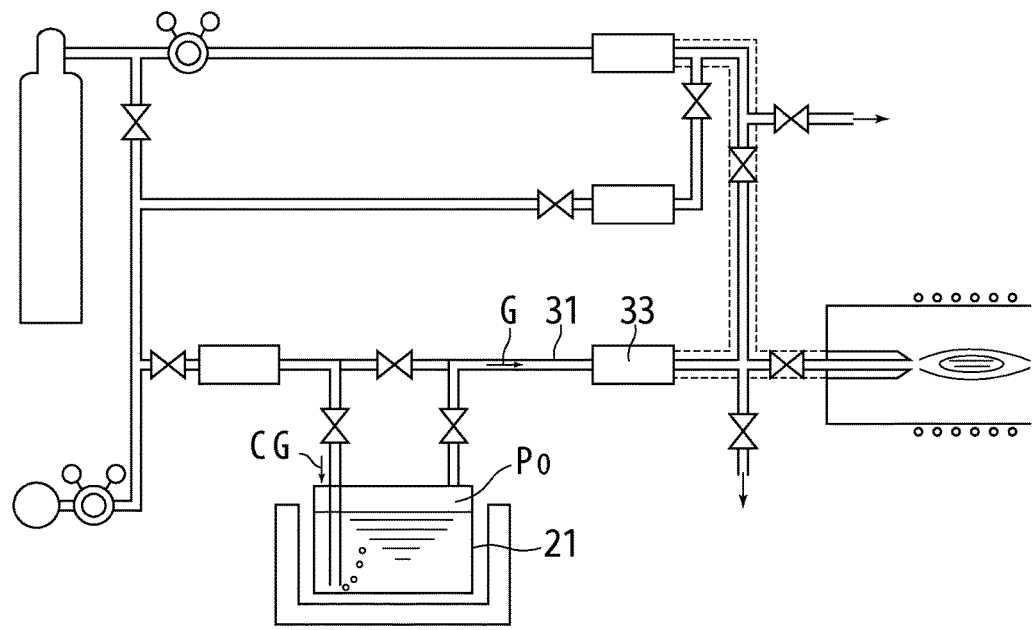
FIG. 11 A systematic view showing an example of use of another former gas density meter.

First, as illustrated in FIG. 8, the raw material fluid density detector 1 was connected to a supply pipe line of process gas (Organic raw material TMGa steam) for semiconductor manufacturing apparatus in the in-line shape, and then light was emitted to the light oscillation unit 5a through the optical fiber 9 from a light source device 18. The photodiodes 10 of the light oscillation unit 5a and the light detection unit 5b are set to a right receiving surface having a size of 1.0 mm×1.1 mm, a diameter of 504 mm, and a height of 3.6 mm. The sapphire light transmission plate 11a is set to a thickness of 1.0 mm and a diameter of 8.0 mm. The length of the flow path length 2b between the light oscillation unit 5a and the light detection unit 5b is set to 30 mm and the internal diameter of the flow path is set to 4.0 mmφ.

Light is emitted to the light oscillation unit 5a, a detection output from the photodiode 10 of the light oscillation unit 5a is input into the arithmetic calculation device 19 through a reflected light detection device 18a and also a detection output from the photodiode 10 of the light detection unit 5b is input into the arithmetic calculation device 19 through an output photon detection device 18b, the density of the organic raw material TMGa steam flowing in the fluid flow path 2a is calculated herein at predetermined time intervals using Expression (1), and then the results are recorded and displayed.

The detection output from the reflected light detection device 18a is used for compensation of the raw material density detection value in the arithmetic calculation device 19. Thus, a measurement error of the raw material density due to so-called fluctuation of the incident light from the light source device 18, changes with time in the light transmittance of the sapphire light transmission plate 11a, and the like is corrected.

It is confirmed from the test results that the raw material fluid density detector according to the present invention enables high-accuracy density measurement which is not inferior to a former expensive density detection meter.

INDUSTRIAL APPLICABILITY

The present invention can be used not only for a gas supply system for semiconductor manufacturing but for continuous detection of the fluid density in every fluid supply line and fluid use apparatus treating a depositing, photoreactivity, and corrosive fluid.

REFERENCE SIGNS LIST 1 raw material fluid density detector
2 detector main body
2a fluid flow path
2b fluid flow path
2c fluid flow path
3 inlet block
3a fluid flow path
3b coupling portion
4 outlet block
4a fluid flow path
4b coupling portion
5a light oscillation unit
5b light detection unit
6 gasket type seal
6a gasket
6b ring-like retainer
6c guide ring
7 leakage inspection hole
8 fixation bolt
9 optical fiber
9an optical fiber insertion hole
10 photodiode
11 plate member (light transmission window) containing brittle fracture material
11a sapphire light transmission plate
12 holding and fixing body
12a flange accommodation portion
12b bolt insertion hole
12c step portion
13 seal surface
14 first fixing flange
14a step portion
14b insertion recess
14c bottom surface (seal surface) of recess
14d gasket accommodation portion
16 second fixing flange
16a step portion
16b projection portion
16c photodiode accommodation recess
16d tip surface (seal surface) of projection portion
17 recess
17a gasket accommodation portion
18 light source device
18a reflected light detection device
18b output light detection device
19 arithmetic calculation device
20 standard density meter

What is claimed is:

1. A raw material fluid density detector of an optical-analysis-type, comprising:
a detector main body; and
a light oscillation unit and a light detection unit provided on an upper surface or an undersurface of the detector main body,
the detector main body including:
at least one recess formed in each of the upper surface and the undersurface of the detector main body,
a fluid flow path connecting a fluid inlet of the detector main body to the recess,
a fluid flow path connecting the recesses to each other, and
a fluid flow path connecting the recess to a fluid outlet of the detector main body, wherein
the light oscillation unit is disposed in at least one recess, and
the light detection units is disposed in the remaining recess.

2. The raw material fluid density detector according to claim 1, wherein the light oscillation unit includes a light transmission plate, a photodiode for light intensity detection, and a light source (optical fiber) for light oscillation, and wherein the light detection unit includes a light transmission plate and a photodiode for light intensity detection.

3. The raw material fluid density detector according to claim 2, wherein the light transmission plates disposed in the recesses formed in the detector main body are airtightly fixed using gasket type seals.

4. A raw material fluid density detector of an optical-analysis-type, comprising:
  a detector main body;
  a light oscillation unit provided on an upper surface of the detector main body;
  a light detection unit provided on an undersurface of the detector main body;
  recesses provided in the upper surface and the undersurface of the detector main body and connected to each other through a fluid flow path;
  gasket type seals attached into the recesses;
  a first fixing flange and a second fixing flange disposed facing the gasket type seals and airtightly joined and fixed while holding the light transmission plates;
  an optical fiber and a photodiode provided in the second fixing flange; and
  a holding and fixing body which airtightly fixes both the joined-and-fixed fixing flanges into the recesses of the detector main body through the gasket type seals.

5. A raw material fluid density detector of an optical-analysis-type, comprising:
  a detector main body;
  a light oscillation unit provided on an upper surface of the detector main body; and
  a light detection unit provided on an undersurface of the detector main body,
  the detector main body including:
    a recess provided in each of the upper surface and the undersurface of the detector main body,
    a fluid flow path connecting both the recesses,
    a fluid flow path connecting a fluid inlet to the recess in the upper surface, and
    a fluid flow path connecting a fluid outlet to the recess in the undersurface; and
  the light oscillation unit and the light detection unit each including:
    a gasket type seal attached into a gasket accommodation portion linked to the recess,
    a first fixing flange including an insertion recess having an inner circumferential surface with a stepwise narrowed diameter and disposed facing the gasket type seal,
    a light transmission plate disposed at a deepest portion of the insertion recess of the first fixing flange,
    a second fixing flange airtightly joined and fixed to the first fixing flange while sandwiching the light transmission plate by insertion of a projection portion having a step-like outer circumferential surface into the insertion recess of the first fixing flange,
    a photodiode for light intensity detection disposed and fixed on an outside of the light transmission plate in the second fixing flange, and
    a holding and fixing body including a flange accommodation portion accommodating both the joined-and-fixed fixing flanges at a center portion and airtightly fixing both the fixing flanges accommodated in the flange accommodation portion to the detector main body through the gasket type seal by cramping a fixation bolt.

6. The raw material fluid density detector according to claim 5, wherein a tip surface of the projection portion of the second fixing flange and a bottom surface of the insertion recess of the first fixing flange serve as a seal surface of the light transmission plate.

7. The raw material fluid density detector according to claim 5, a bottom surface of the gasket accommodation portion of the first fixing flange serves as a gasket seal surface.

8. The raw material fluid density detector according to claim 5, wherein
  an optical fiber insertion hole is provided in the second fixing flange of the light oscillation unit, and
  the photodiode serves as a photodiode for detecting an intensity of reflected light from the light transmission plate.

9. The raw material fluid density detector according to claim 5, wherein the photodiode provided in the second fixing flange of the light detection unit serves as a photodiode for detecting an intensity of transmission light from the light transmission plate.

10. The raw material fluid density detector according to claim 5, wherein
  another light detection unit is provided at an interval on the upper surface of the detector main body,
  the recess of the light detection unit provided in the undersurface of the detector main body and the recess of the other light detection unit are connected to each other through the fluid flow path, and
  an intensity of reflected light from the light transmission plate of the light detection unit provided on the undersurface is detected in the another light detection unit.

11. The raw material fluid density detector according to claim 5, wherein the raw material fluid is a depositing, high reactive, or corrosive organic raw material.

12. The raw material fluid density detector according to claim 5, wherein the light transmission plate is formed of sapphire.

* * * * *